United States Patent
Khutoryansky et al.

[11] Patent Number: 6,047,042
[45] Date of Patent: Apr. 4, 2000

[54] AUTOMATIC EXPOSURE AND BRIGHTNESS CONTROL FOR FLUOROSCOPIC AND RADIO-GRAPHIC IMAGING

[75] Inventors: Oscar Khutoryansky, Glenview; Thomas Rosevear, Elmhurst; Yevgeniy Maltsev, Skokie; Thomas Simak, Warrenville; Gregory Pasman, Skokie, all of Ill.; James A. Princehorn, Sandyhook, Conn.

[73] Assignee: Continental X-Ray Corporation, Broadview, Ill.

[21] Appl. No.: 09/047,535

[22] Filed: Mar. 25, 1998

[51] Int. Cl.[7] .................................................. G01N 23/04
[52] U.S. Cl. ............................................ 378/62; 378/98.8
[58] Field of Search ............................. 378/62, 98.7, 96, 378/97, 108, 116, 98.8

[56] References Cited

U.S. PATENT DOCUMENTS

| | | | |
|---|---|---|---|
| 4,247,777 | 1/1981 | Pfeifer et al. | 250/416 R |
| 4,454,606 | 6/1984 | Relihan | 378/97 |
| 5,333,168 | 7/1994 | Fernandes et al. | 378/108 |
| 5,617,462 | 4/1997 | Spratt | 378/98.7 |
| 5,692,507 | 12/1997 | Seppi et al. | 128/653.1 |

*Primary Examiner*—David V. Bruce
*Assistant Examiner*—Michael J. Schwartz
*Attorney, Agent, or Firm*—Laff, Whitesel & Saret, Ltd.

[57] ABSTRACT

An exposure control system for radiographic, fluoroscopic, or other diagnostic imaging includes an exposure sensor array and a control element. The exposure sensor array has a plurality of sensor elements directed to defined locations uniformly distributed over the imaging field and may make direct or indirect measurements of exposure rate or imaging converter brightness. A structure or region of diagnostic interest to examining personnel is identified, and only sensors which correspond to locations within the area of interest are selected for use in exposure control. Predefined examination parameters suitable for particular anatomical patient regions are stored. Upon request by examining personnel to perform an examination of an anatomical patient region, the parameters are retrieved for use. The parameters include a preselection of sensors typically suitable for examinations of such region. The sensor locations, and their selection status, may be displayed as an overlay on an actual diagnostic image so that examining personnel may determine which sensors correspond to a structure or region of diagnostic interest. Examining personnel may manually select or deselect sensors. During an automatic mode examination, sensor outputs are analyzed and sensors providing apparently spurious outputs are deselected.

32 Claims, 7 Drawing Sheets

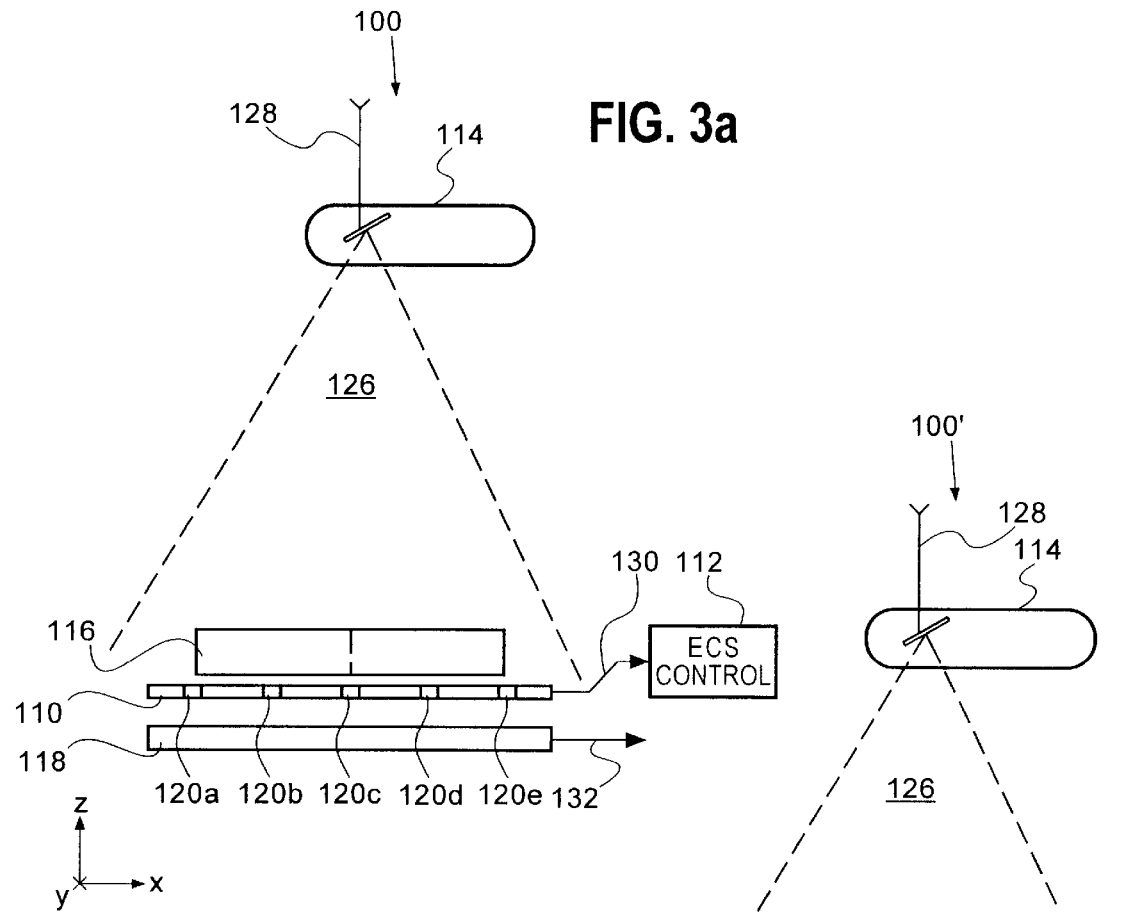
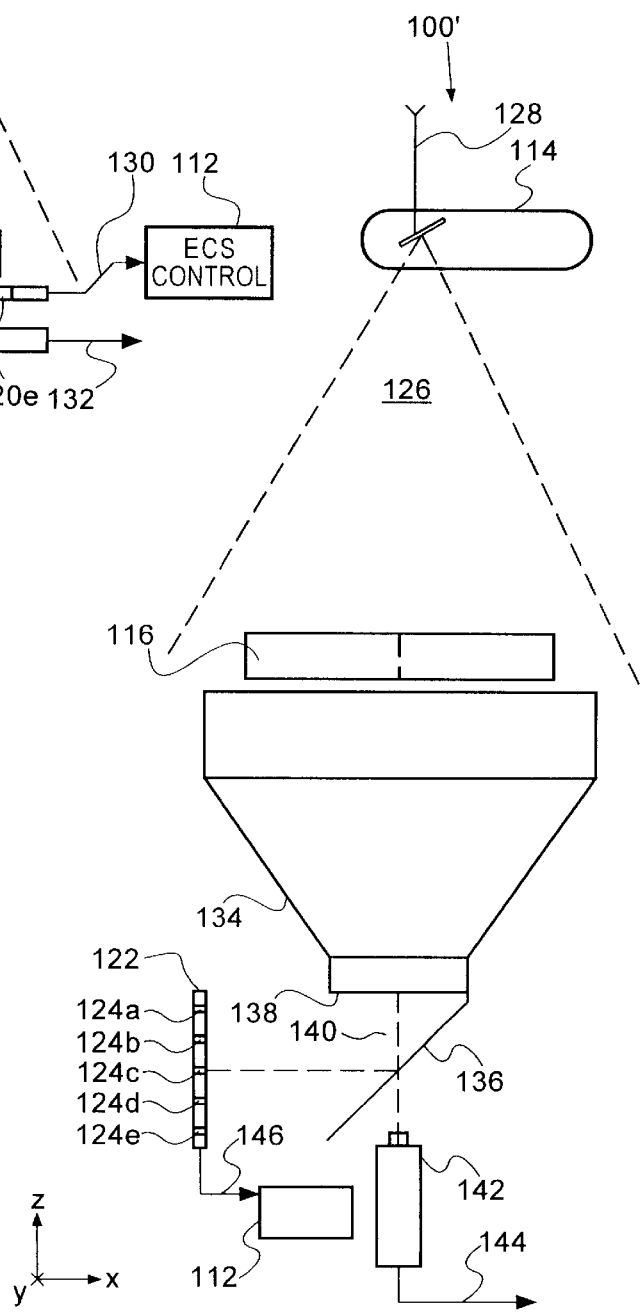

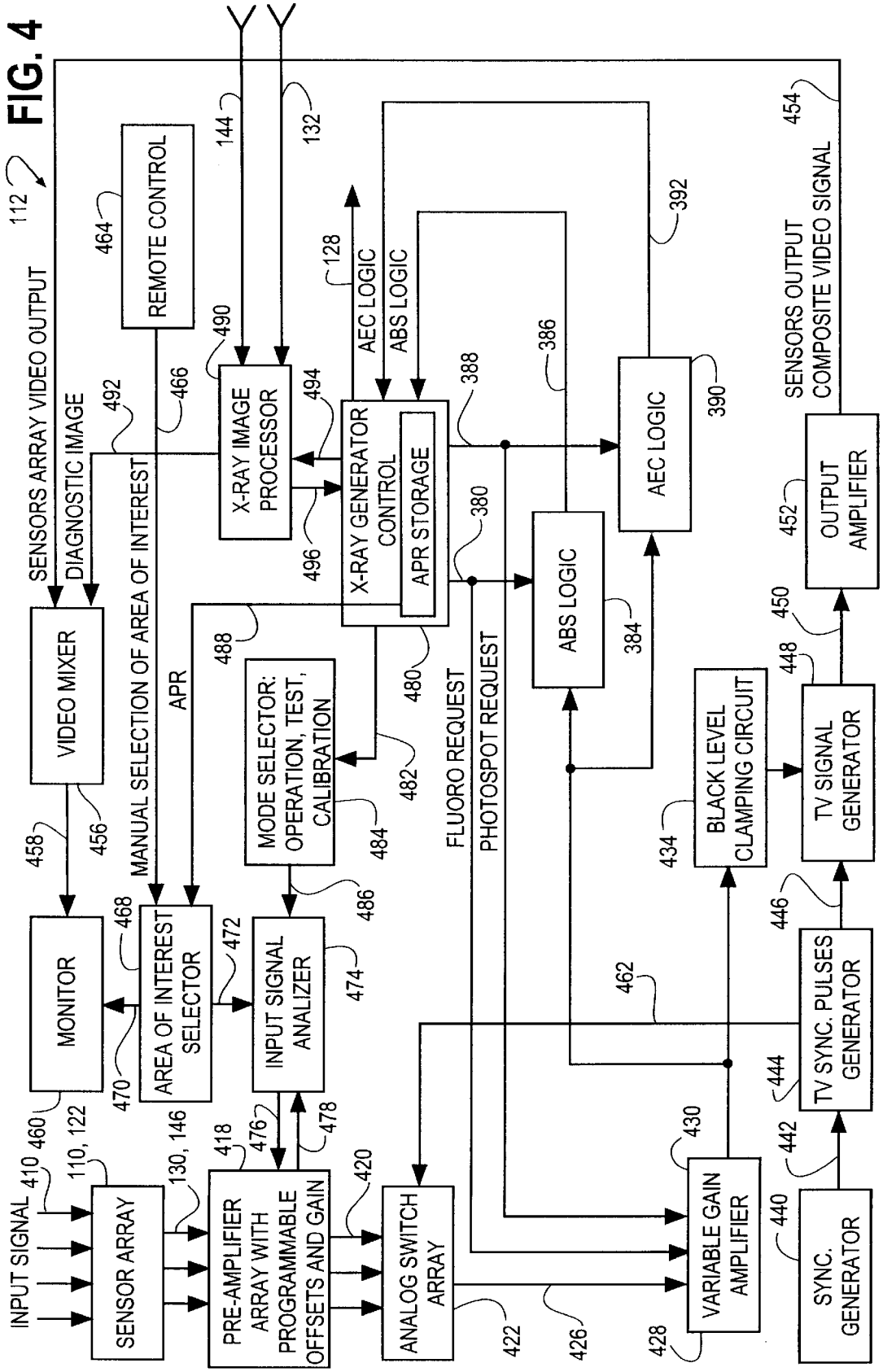

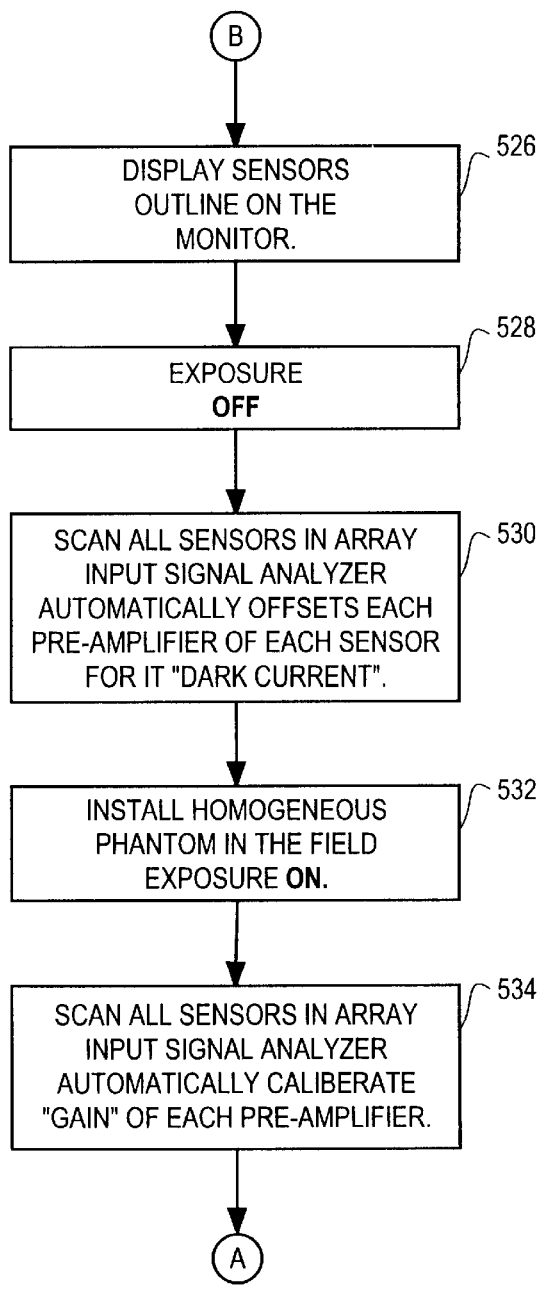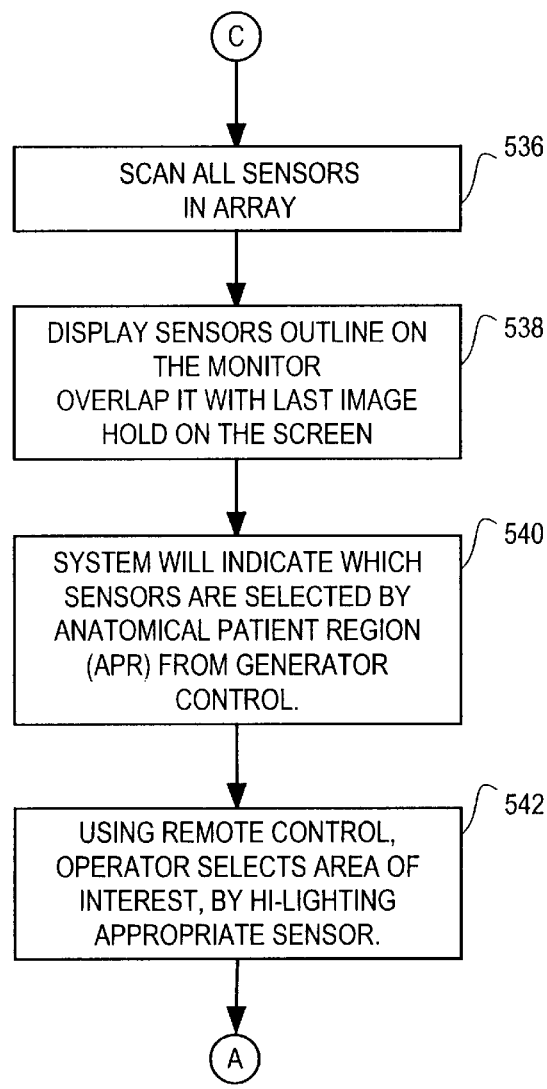

AUTOMATIC EXPOSURE AND BRIGHTNESS CONTROL FOR FLUOROSCOPIC AND RADIO-GRAPHIC IMAGING

FIELD OF THE INVENTION

This invention relates to medical diagnostic imaging systems, and more particularly to radiographic and fluoroscopic imaging systems incorporating automatic exposure controls and automatic brightness systems in order to provide proper exposure despite variations in object density and position.

BACKGROUND OF THE INVENTION

Despite the introduction in recent years of several new diagnostic imaging modalities, traditional methods of producing diagnostic images, such as transmission radiography and fluoroscopy, remain popular, as they are cost-effective and diagnostically useful. In both radiography and fluoroscopy, a source of penetrating energy, such as X-rays, is directed to illuminate a volume of interest within the patient. An imaging receptor, such as photographic film or an image intensifier, is positioned opposite the source to receive the penetrating energy transmitted through the volume of interest. Differential attenuation by various elements of the volume of interest, due to variations in the length of the imaging energy path through the object, and in the density of the material along that path, results in corresponding amounts of imaging energy striking the various locations of the imaging receptor. By recording the amount of imaging energy striking such locations, an image corresponding to structures internal to the volume of interest may be produced.

When X-rays or other potentially dangerous sources of penetrating energy are used to produce an image, it is essential that the dose to the patient be minimized. At the same time, it is an objective to acquire an image of high diagnostic quality. Typical imaging receptors include photographic film, electronic image-intensifier/camera chains, and solid state imaging receptors. Although the characteristics of these receptors vary, all of them have limited dynamic range, and overexposure or underexposure may produce a poor quality or unusable image. Accordingly, in order to produce a high-quality diagnostic image, while minimizing the dose to the patient, proper selection of exposure parameters is essential. An improper exposure resulting in a diagnostically unusable image, is particularly disadvantageous, because repeating the examination necessarily involves additional exposure of the patient to X-rays or another energy source.

Historically, radiologists or skilled examination technicians have selected the exposure parameters based on observed or measured characteristics of the patient volume being imaged (e.g., the thickness of the portion of the patient to be imaged), with the help of published tables and empirically derived knowledge of how particular anatomical features should be exposed for best results. A number of disadvantages result from the selection of all exposure parameters solely by human operators, because the operators may make mistakes. For example, the operator may erroneously determine or observe a physical parameter of the patient or the imaging path, erroneously select a parameter from a publication or table, or make a calculation error.

A number of automatic exposure control (AEC) systems have been developed for use in improving exposure control in radiography applications. Conventional AEC systems allow the operator to specify a desired exposure (or dose) in terms of the dose rate integrated over time. A sensor is positioned near, and typically in front of, the image receptor to measure the imaging energy incident thereon throughout the examination. During the exposure, the AEC system determines the accumulated exposure amount (for example, by integrating the instantaneously-measured dose rate over time) and terminates the exposure when the accumulated value reaches that specified by the operator. Such systems are sometimes referred to as "phototimer detectors."

Similarly, automatic brightness systems (ABS) have been developed for use in improving exposure control in fluoroscopy applications. Conventional ABS systems attempt to control the instantaneous exposure rate to achieve a consistent, predetermined exposure level (or "brightness"), averaged across the image. If an image intensifier (or some other image receptor which produces a physically observable image) is used, a sensor may be provided to observe the image screen and directly measure its brightness. Alternatively, an output signal from the image receptor may be used to measure the image brightness. The ABS uses the image brightness measurement to control an exposure rate parameter of the imaging energy source as necessary to achieve the desired average brightness over the image. Conventional ABS systems used in conjunction with fluoroscopy systems, in which the source is an X-ray tube, typically control the X-ray tube high-voltage. However, other parameters may also be used to control the exposure rate, and still other parameters could be used to adjust the sensitivity or dynamic range of the imaging receptor.

Although both AEC and ABS systems have been advantageously applied to reduce patient exposure and improve diagnostic image quality, existing systems exhibit several deficiencies. In most imaging applications, the region of diagnostic interest to the physician does not fill the entire image field. It is often difficult in advance to precisely position the patient with respect to the imaging equipment such that an anatomical feature or region of interest lies entirely within the image field and substantially fills the field. Accordingly, the image field is typically selected to be somewhat larger than the feature of interest so that the entire feature will lie within the image even if initial misalignment or subsequent patient movement occur. Existing AEC systems in which an ion chamber or similar exposure sensor is used typically measure exposure rate or image brightness at one, two, or three predefined locations within the image field. Existing ABS and AEC systems in which an image intensifier is used as the imaging receptor typically measure exposure rate or image brightness over portion of the image field ranging from 30–60 percent of the area of the field. For example, phototimer detectors are frequently used individually, or in pairs or triplets, to sample several areas of the radiographic field. In systems designed for PA chest imaging (in which a front-to-back chest image is desired), paired detectors may be used.

An exposure measurement error will occur whenever the anatomical structure or region of interest does not completely cover the entire field of the exposure measuring sensor. The size and locations of the measuring fields in conventional AEC/ABS systems are fixed. It may be difficult or impossible prior to exposure to position the patient such that the anatomical structure or region of diagnostic interest accurately corresponds to the measurement location or locations used by the AEC/ABS systems. This is especially the case if the anatomical structure or region of interest is irregularly shaped or is small with respect to the volume of the patient. Thus, conventional AEC/ABS systems may undesirably respond to exposure measurements outside the region of diagnostic interest, and in some cases, the exposure measurement locations may lie entirely outside the region of diagnostic interest. This results in exposure measurement errors. Such errors will be large if the attenuation due to the portion of the imaged object which lies in the exposure measurement field differs significantly from the attenuation due to the region of interest.

For example, in imaging examinations involving the extremities of the body, such as the hand, arm, or shoulder, the structure of interest may only partially cover the exposure sensor field. As a result, unattenuated radiation reaches the sensor, and the sensor erroneously includes this radiation in its measurement of the exposure rate. If a radiographic exposure is being conducted under AEC, the exposure is terminated early, and the structure or region of interest will be under-exposed. If a fluoroscopic exposure is being conducted under ABS, the ABS reduces the X-ray tube voltage such that the average image brightness, including the artificially bright portion of the image corresponding to the uncovered portion of the exposure sensor field, approaches the predetermined target brightness. As a result, the structure or region of interest will be artificially darkened. Even if the image of the region of interest remains usable, its diagnostic quality is substantially reduced.

The problem of aligning the structure or region of interest with the exposure sensor field is compounded by the need to perform examinations involving relative motion between the patient and the imaging system. Even if good alignment is initially achieved, relative motion may move the exposure sensor out of alignment with the structure or region of interest, although the structure may remain within the image field. Each relative motion step effectively selects a new structure or region of interest, at which the patient geometry or other characteristics may vary. Thus, at a subsequent imaging position, the selected structure or region of interest may no longer be aligned or sized to correspond with the exposure sensor field. For example, in a peripheral angiography examination of a patient's leg, at a first position, the structure or region of interest may completely fill the exposure sensor field. At a subsequent position, the leg may be thinner, or the orientation of the leg may be different, such that the structure or region of interest does not fill the sensor field, or the sensor field is partially uncovered.

OBJECTS AND SUMMARY OF THE INVENTION

It is therefore an object of the present invention to provide an exposure control system for use with a diagnostic imaging system which avoids the aforementioned disadvantages of the prior art.

It is another object of the present invention to provide an exposure control system which minimizes exposure measurement errors.

It is a further object of the invention to provide an exposure control system which permits selection and use of an exposure measurement region that closely corresponds to an examination region of interest.

It is another object of the invention to provide an exposure control system which detects and eliminates from use exposure measurements from locations outside an examination region of interest.

It is a further object of the present invention to provide an exposure control system which detects spurious exposure measurements and eliminates such spurious measurements from use.

It is another object of the invention to provide an exposure control system for use in radiographic and fluoroscopic examinations wherein the exposure measurement regions for each type of examination closely correspond to one another.

According to the present invention, an exposure control system for use with a diagnostic imaging system includes one or more sensors for providing exposure measurements corresponding to a plurality of defined locations or regions on an imaging receptor of the imaging system. A control element permits manual or automatic selection of which sensors are to be used in exposure control. By selecting for use in exposure control those sensors which closely correspond to the geometry of the structure or region of interest, the exposure characteristics of the structure or region of interest may be optimized, and exposure errors due to anomalous conditions outside the structure or region of interest may be minimized.

For use with radiographic imaging systems, the sensor preferably comprises a radiographically transparent array of sensor elements disposed between the patient imaging position and the imaging receptor to directly measure the X-radiation incident on the imaging receptor at the defined locations or regions. The elements of the radiographic exposure sensor array may be implemented using ion chambers, photo-diodes, photo-transistors, fluorescent detectors with optical light followers, or other known X-ray detector elements. Other types of detector elements could also be used.

For use with fluoroscopic imaging systems, the sensor preferably comprises an array of optical detectors disposed to receive from an X-ray-to-optical-light conversion component of the imaging receptor image information corresponding to the defined image locations or regions. Many fluoroscopic imaging systems incorporate "image intensifier systems" which convert incident X-radiation to an optical light image which may be viewed directly or converted to a representative electrical signal using a video camera or its equivalent. The elements of the fluoroscopic exposure sensor array may be implemented using an array of phototransistors; an optical splitter may be used to route the optical image from the image intensifier to both the camera and the exposure sensor array. Other types of detector elements could also be used.

In diagnostic imaging systems which provide both radiographic and fluoroscopic examinations, the radiographic and fluoroscopic exposure sensor arrays are preferably arranged to provide respective sensor elements directed to closely corresponding locations in both images.

The exposure control system includes control components for receiving control inputs from examining personnel, displaying information to examining personnel, receiving and analyzing sensor information, and for controlling exposure parameters responsively. According to an aspect of the invention, the exposure control system provides facilities to allow examining personnel to select specific sensor elements or sensor locations to be used for exposure control. The examining personnel may, for example, select for use in exposure control those sensors or sensor locations which correspond to the structure or region of interest as portrayed in an acquired image.

According to another aspect of the invention, the exposure control system provides facilities to receive from examining personnel a selection of an anatomical patient region to be examined, and in response thereto, select appropriate sensors for use in exposure control during an examination of such a region. The exposure control system preferably has facilities to display an image acquired from the patient, to identify thereon the locations to which sensors correspond, and to identify thereon which sensors are selected.

According to a further aspect of the invention, the exposure control system provides facilities to evaluate the exposure or brightness measurements from each sensor element or location in order to determine whether measurements from such sensor should be used in exposure control or discarded. For example, if the measurement from the sensor is above or below predefined limits (as may happen when the patient covers only part of the imaging receptor), the system may determine that the measurement is likely to introduce error and should not be used. The exposure control system may also provide automatic calibration of the gain and offset of each sensor measurement circuit.

BRIEF DESCRIPTION OF THE DRAWINGS

These and other features of this invention will be best understood by reference to the following detailed description of a preferred embodiment of the invention, taken in conjunction with the accompanying drawings, in which:

FIG. 3a is a front elevation view of the inventive exposure control system of FIG. 1;

FIG. 3b is a front elevation view of a second preferred embodiment of the inventive control system of FIG. 1, showing an arrangement of components suitable for controlling both radiographic and fluoroscopic exposures;

FIG. 4 is a block diagram showing the arrangement of a control component for use with the exposure control system of FIGS. 1–3;

FIGS. 5a–5d form a flow diagram showing a method of operation for use with the exposure control system of FIGS. 1–4.

DETAILED DESCRIPTION OF THE PREFERRED EMBODIMENT

FIGS. 1–6 generally show preferred embodiments 100, 100' of an exposure control system (ECS) constructed according to the present invention for use in conjunction with a diagnostic imaging system capable of radiographic and/or fluoroscopic examinations.

FIGS. 1–3a show a first preferred embodiment 100 of the ECS adapted for use in controlling radiographic exposures. FIG. 3b shows a second preferred embodiment 100' of the ECS adapted for use in controlling both radiographic and fluoroscopic exposures. For convenient reference, a set of orthogonal coordinate axes, labeled X, Y, and Z, is defined. References herein to the X, Y, or Z directions mean a direction parallel to the respective coordinate axis. The first and second preferred embodiments 100, 100' are essentially the same, with the exception that the first embodiment 100 contemplates the use of an imaging receptor 118 adapted primarily for acquiring radiographic images, while the second embodiment 100' contemplates the use of an imaging receptor 134 adapted for recording both radiographic and fluoroscopic images. Accordingly, the first and second embodiments of the ECS 100, 100' will generally be described collectively as to structures, features, and characteristics common to both, with an explanation of differences provided where necessary. Like reference numbers indicate equivalent elements or steps in each embodiment.

Figure 1:
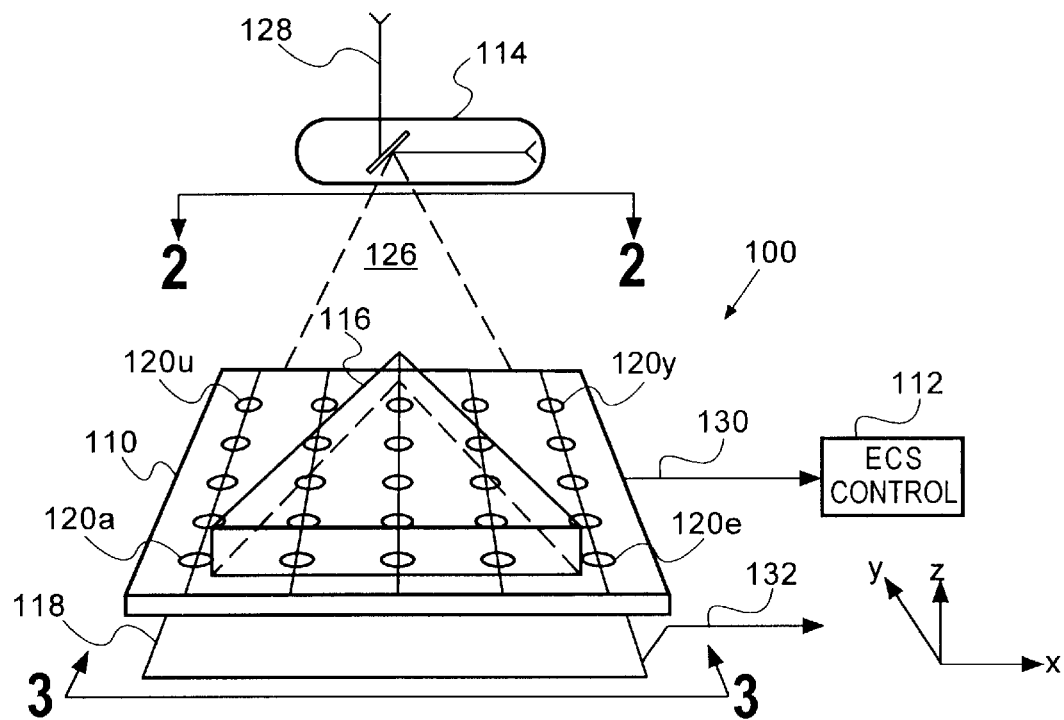
FIG. 1 is a simplified partial front perspective view/partial block diagram of a first preferred embodiment of an exposure control system constructed according to the present invention, for use in conjunction with a diagnostic imaging system, showing the arrangement of an exposure sensor array for use therewith in controlling radiographic exposures.
Figure 2:
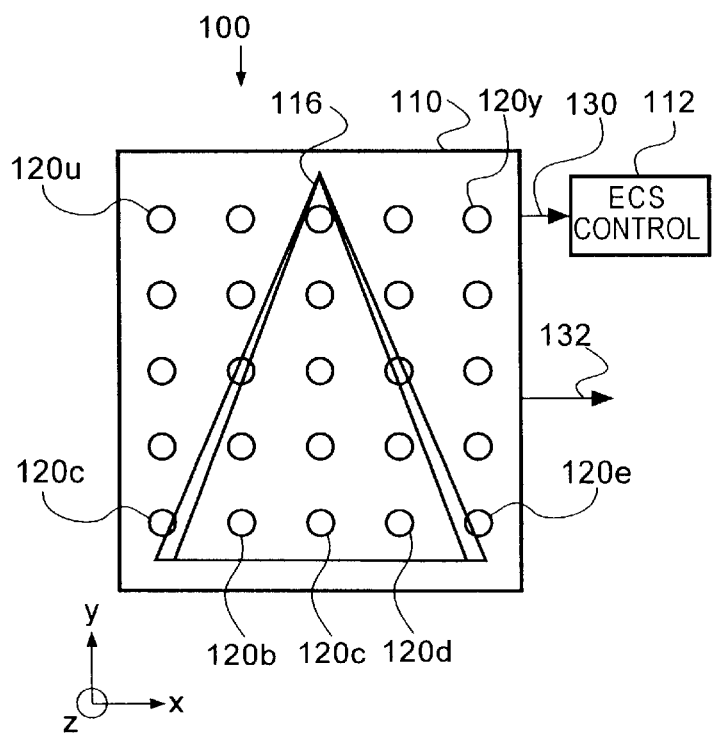
FIG. 2 is a top plan view of the inventive exposure control system of FIG. 1, showing the relationship of the exposure sensor array to an anatomical structure to be examined.
Figure 5A:
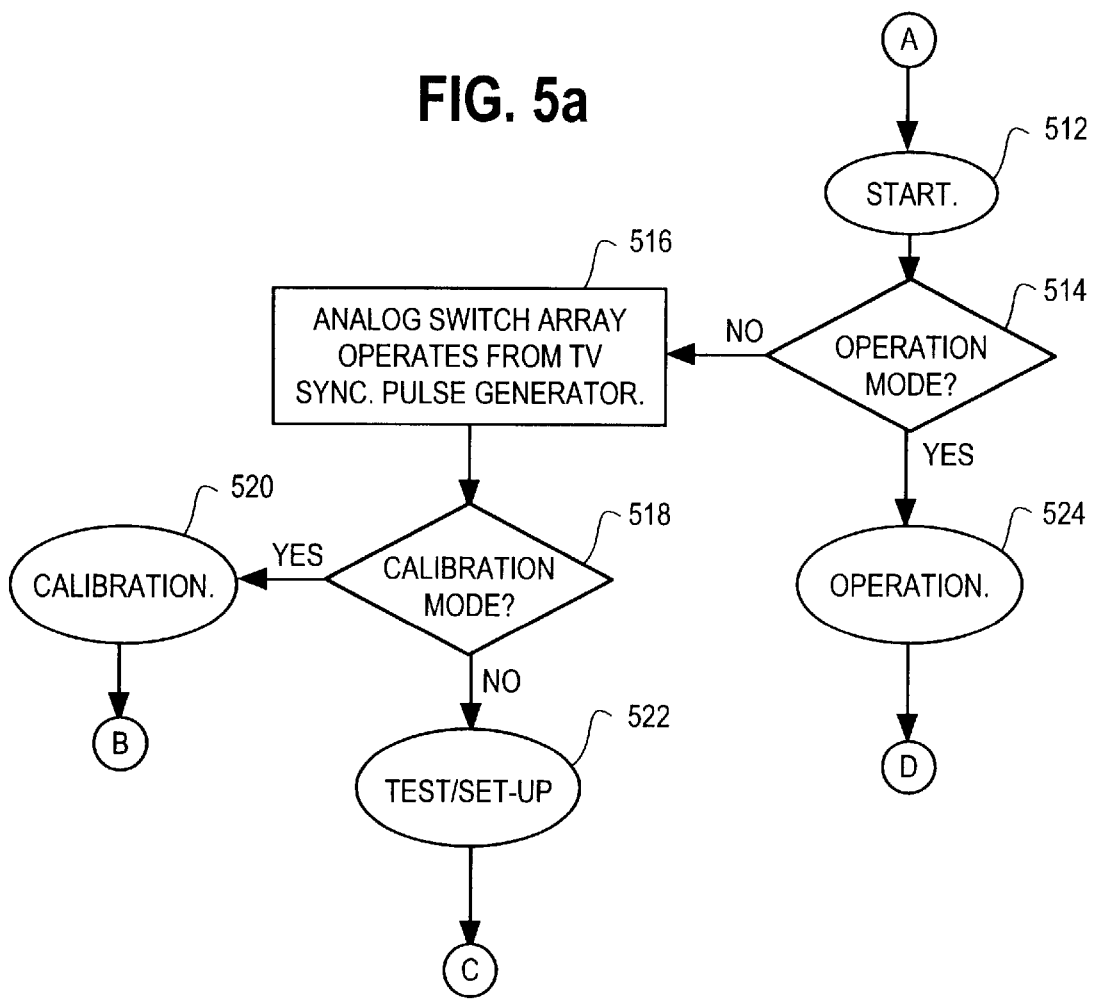
Figure 5D:
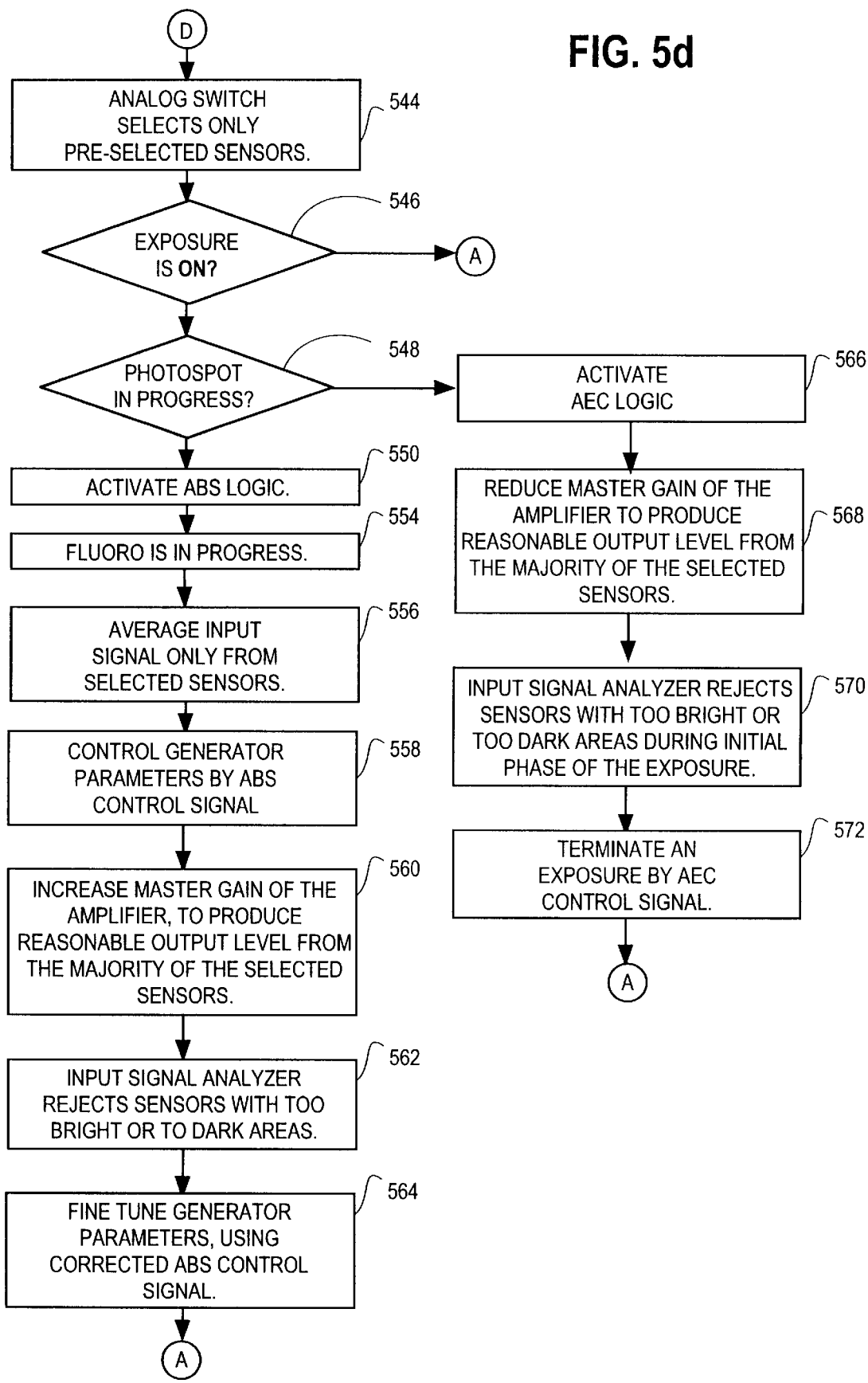
Figure 6:
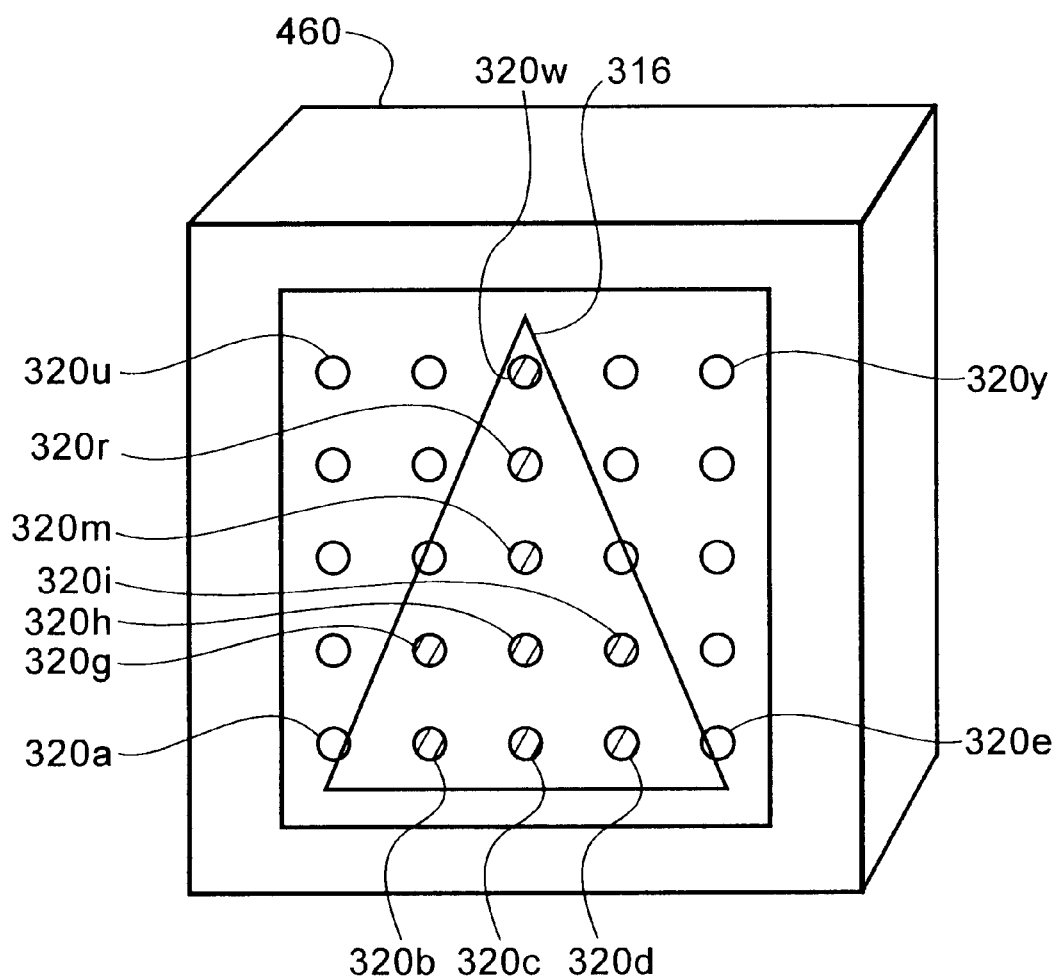
FIG. 6 is a simulated view of a monitor of a diagnostic imaging system, depicting its display of an acquired image showing the locations of exposure sensors superimposed thereon, and identifying selected sensors, as such an image would be generated by the control component of FIG. 4 operating according to the method of FIGS. 5a–5d.

FIG. 4 is a block diagram showing the arrangement of a control element 112 for use in controlling both embodiments 100, 100'. Some elements shown in FIG. 4 are not necessary for use in controlling the first embodiment 100 and may be omitted (discussed below in greater detail). FIGS. 5a–5d are a flow diagram showing a method 510 of operating the ECS 100, 100', for use in conjunction with the control element 112. FIG. 6 shows a monitor display which would be produced by the control element 112 under the method 510 of FIG. 5, showing an acquired image with the locations of exposure sensors superimposed thereon.

Consistent with the spirit of the present invention, the "signals" and "signal paths" described herein may take a number of forms depending on how certain components of the inventive ECS 100, 100' are implemented. For example and without limitation, a particular "signal" could be an optical signal, an analog electrical signal, a digital electrical signal (including a related group of digital signals forming a bus), or a stream or collection of data representing a physical quantity, value, or event. Accordingly, although certain signals may be described herein in connection with an exemplary form, one of skill in the art will appreciate that the signals may take other forms without departing from the invention. Moreover, for convenience hereafter, signals, and the signal paths which carry them, generally will be referred to interchangeably.

As best seen in FIGS. 1–3a and 3b, an ECS 100, 100' constructed according to the present invention may be used advantageously with a diagnostic imaging system employing penetrating energy in connection with which it is desired to control exposure for minimum patient dose and maximum image quality. The imaging system preferably comprises a source 114 for producing penetrating imaging energy 126 directed toward a suitable image receptor 118 (FIG. 3a) or 134 (FIG. 3b). In diagnostic imaging systems which employ X-rays as the imaging energy, the source 114 may be an X-ray tube or other appropriate source. The image receptor may be conventional film or a planar electronic detector 118, as best seen in FIG. 3a, or may be an image intensifier 134, as best seen in FIG. 3b. If the imaging receptor 118 is implemented as an electronic detector, a signal representing the acquired image is preferably supplied to the control element 112 (and other imaging system components) on lead 132. The planar electronic detector 118 may be implemented as a flat panel detector, which, for example, may be constructed of amorphous silicon coated with selenium or a fluorescent material. Other suitable flat panel detectors could also be used. If the imaging receptor is implemented as an image intensifier 134, a signal representing the acquired image may be generated by a suitable video camera 142 (or another appropriate apparatus for converting an optical image into a usable signal) and supplied to the control element 112 (and other imaging system components) on lead 146. Other types of imaging energy, imaging energy sources, and imaging receptors, could also be used. For example, ultrasound or infrared imaging energy sources, and corresponding imaging receptors, may be used.

A portion of a patient's body containing a structure or region of interest 116 for which an image is desired is interposed between the source 114 and the image receptor 118, 134 preferably at a location near the receptor for illumination by the imaging energy 126. The structure or region of interest (SRI) 116 is shown for simplicity in FIGS. 1–3 as a triangular-prism shaped object, which is intended to represent a limb, an internal anatomical structure, or a region within the body. As best seen in FIGS. 1–3b, the ECS 100, 100' preferably comprises one or more appropriate sensor arrays 110 (FIGS. 1–3b) and 122 (FIG. 3b only) for measuring exposure, and an ECS control element 112 for controlling one or more exposure parameters in response to measurements from the sensor arrays 110, 122. Each sensor array 110 and 122 provides facilities for making exposure measurements corresponding to a plurality of defined locations or regions on an associated imaging receptor 118, 134 of the imaging system (discussed below in greater detail). The term "array" is used herein to refer to a plurality of locations corresponding to which individual exposure measurements may be obtained. The sensor "arrays" 110, 122 may be implemented using a plurality of individual sensor elements, but could also be implemented using a single sensor having the capability of delivering individually distinguishable exposure measurements from such plurality of locations.

The control element 112 permits manual or automatic selection of which sensors are to be used in controlling the exposure parameter or parameters. By selecting for use in exposure control those sensor array elements or locations which closely correspond to the geometry of the SRI 116, the exposure characteristics of the SRI 116, may be optimized, and exposure errors due to anomalous conditions outside the SRI 116 may be minimized.

As best seen in FIGS. 1–3a, for use in performing radiographic exposures, a sensor array 110 preferably comprises a radiographically transparent array of sensor elements (e.g., a 5×5 array of elements designated 120a, 120b, 120y) disposed between the SRI 116 and the imaging receptor 118 to directly measure the X-radiation incident on the imaging receptor 118 at each of the defined locations or regions. More or fewer detector elements could be used. The elements 120a–120y of the radiographic exposure sensor array 110 may be implemented using ion chambers, photo-diodes, photo-transistors, fluorescent detectors with optical light followers, or other known X-ray detector elements. Suitable arrays of photo-diodes, formed as relatively small, integrated packages, are commercially available. Other types of detector elements could also be used. The output signal of the sensor array 110 is preferably supplied to the control element 112 on lead 130.

As best seen in FIG. 3b, for use in performing both radiographic and fluoroscopic exposures, a sensor array 110 as described above could be used. Many fluoroscopic imaging systems incorporate "image intensifier systems" (e.g. 134 (FIG. 3b) which convert incident X-radiation to an optical light image on a screen 138 which may be viewed directly or converted to a representative electrical signal 144 using a video camera 142 or its equivalent. Where an image intensifier 134 is used as the imaging receptor, an exposure sensor array 122 is preferably arranged to perform exposure measurement by directly observing the brightness of the image produced by the image intensifier 134.

Sensor array 122 preferably comprises an array of optical detector elements (e.g., a 5×5 array of elements designated 124a, 124b, ... 124y) disposed to receive optical image information from an X-ray-to-optical-light conversion component of the imaging receptor, such as screen 138. Each optical detector element preferably corresponds to a respective one of the defined image locations or regions of the imaging receptor. More or fewer detector elements could be used. The optical detector elements 124a–124y of the fluoroscopic exposure sensor array 122 may be implemented using an array of photodiodes or phototransistors. In particular, suitable photodiode arrays are widely commercially available in integrated packages, and, in some cases, are constructed on a single substrate. This provides consistent measurements from each sensor element and may reduce the effort required to calibrate the array. Any other suitable optical detector means, such as photomultipliers, photodiodes, or the like, may also be used. An optical splitter 136 may be used to route the optical image 140 from the image intensifier screen 138 to both the camera 142 and the exposure sensor array 122. The output signal of the sensor array 122 is preferably supplied to the control element 112 on lead 146.

If separate radiographic and fluoroscopic exposure sensor arrays 110 and 122 are provided, the radiographic and fluoroscopic exposure sensor arrays 110, 122 are preferably arranged to provide respective sensor elements directed to closely corresponding locations in both images.

The ECS 100, 100' comprises a control element 112 and associated components for receiving control inputs from examining personnel, displaying information to examining personnel, receiving and analyzing sensor information, and for controlling exposure parameters responsively.

According to an aspect of the invention, the control element 112 provides facilities to allow examining personnel to select specific sensor elements or sensor locations to be used for exposure control. The examining personnel may, for example, select for use in exposure control those sensors or sensor locations which correspond to the structure or region of interest as portrayed in an acquired image.

According to another aspect of the invention, the control element 112 provides facilities to receive from examining personnel a selection of an anatomical patient region to be examined, and in response thereto, select appropriate sensors for use in exposure control during an examination of such a region. The control element 112 preferably has facilities to display an image acquired from the patient, to identify thereon the locations to which sensors correspond, and to identify thereon which sensors are selected. For example, the control element 112 may display from storage the last image acquired from the patient, with the position and status of each sensor overlayed on the image.

According to a further aspect of the invention, the control element 112 provides facilities to allow automatic or manual selection of a sensor weighting or aggregation mode, according to which measurements from one or more sensors are used in controlling or terminating an exposure. For example, the control element 112 may use the average of measurements from a plurality of selected sensors to control or terminate an exposure. Alternatively, the control element 112 may employ only the measurement from one selected sensor producing the largest exposure measurement value (or several high-output-value sensors), in order to avoid over-exposing any particular portion of the image.

According to another aspect of the invention, the control element 112 provides facilities to evaluate the exposure or brightness measurements from each sensor element or location, or any combination of them, in order to determine whether measurements from such sensor element or location should be used in exposure control or discarded. For example, if the measurement from the sensor is above or below predefined limits (as may happen when the patient covers only part of the imaging receptor), the control element 112 may determine that the measurement is likely to introduce error and should not be used. The exposure control system control element 112 may also provide automatic calibration of the gain and offset of each sensor measurement circuit.

FIG. 4, is a block diagram showing a control element 112 for controlling the ECS 100, 100', and for providing these and other facilities. The components of the control element 112 include signal processing elements, image processing elements, and diagnostic imaging system control elements, the functions and design of which are generally known, and suitable implementations of which are readily available from commercial sources. FIG. 5 is a flow diagram showing a method 510 for use in conjunction with the control element 112 for controlling the ECS 100, 100' (discussed below in greater detail).

As best seen in FIG. 4, an input signal 410 is provided to sensor array 110, 122 for exposure measurement and processing. The form of input signal 410 depends on the location and type of sensor being used. For example, sensor array 110 of FIG. 3a is interposed in the path of the penetrating energy 126 (e.g. X-rays) and directly converts the input signal 410, in the form of incident penetrating energy, to a suitable signal 130 representing the exposure rate. Sensor array 122 of FIG. 3b observes the brightness of the image intensifier screen. In that case, the input "signal" 410 is an optical image, and the sensor array 122 produces a representative output signal 146.

The sensor output signals 130 and 146 are supplied to a preamplifier array 418. The preamplifier array preferably includes sufficient preamplifier channels (not shown) to accommodate signals from each of the plurality of sensor elements 120a–120y, 124a–124y of sensor arrays 110, 122, respectively. Each preamplifier channel preferably has programmable gain and offset controls to allow the preamplifier channel to compensate for variations in the response of each detector element. The preamplifier array 128 provides the preamplifier outputs of the sensors via signal path 478 to input signal analyzer 474. The input signal analyzer 474, inter alia, analyzes the preamplifier sensor outputs to determine preamplifier gain and offset adjustments which are required to normalize sensor response, and applies the adjustments to the preamplifier array 418 via signal path 476. A suitable preamplifier array may be constructed from high-impedance, low-noise amplifiers in integrated-circuit packaging, which are commercially available from several suppliers, including Harris Semiconductor, 1025 W. Nasa Blvd., Melbourne Fla. 32919. A preamplifier array could also be constructed using other amplifier circuits, including those employing discrete components.

The preamplifier sensor output from the preamplifier array 418 is provided to an analog switch array 422 via signal path 420. Analog switch array 422 operates under control of the input signal analyzer 474 and the area of interest selector 468 to enable propagation of the exposure measurement signal produced by each sensor element if: (1) the position of such sensor corresponds to a portion of the image within the selected SRI 116; and (2) the output of such sensor is within a predetermined range of "normal" values. The output signals from sensor elements which satisfy these conditions are passed via signal path 426 to a variable gain amplifier 428. The output signal 430 from the variable gain amplifier 428 is provided to ABS logic unit 384 and AEC logic unit 390 for further use in exposure control. The output signals from sensor elements which do not satisfy these conditions are not used.

The control element 112 comprises facilities to produce a video signal 454 representing the position and status of each sensor element with respect to the diagnostic image. A sync generator 440 generates master synchronization signals 442 which are provided to a TV sync pulse generator 444. The TV sync pulse generator 444 produces television-type synchronization pulses on leads 462 and 446. The synchronization pulses are used to construct television-compatible signals representing the sensors so that the signal may be displayed on a video monitor or the like. Synchronization pulses on lead 462 are provided to analog switch array 422. Analog switch array 422 includes means for determining from the synchronization pulses the current effective video image position (beam position) and for producing an output signal via signal path 426 indicating the status of the exposure sensor corresponding to that position. The "status" information provided via signal path 426 may, for example, include a representation of the exposure level measured by respective sensors, and may also indicate information relating to whether the sensor has been automatically or manually selected or deselected. Variable gain amplifier 428 uses the sensor status signal on signal path 426 to modulate a television signal component 430 to produce an image signal representing the position and status of each sensor. Black level clamping circuit 434 normalizes the level of signal 430 for compatibility with television signal standards.

TV signal generator 448 combines the output 446 from TV sync pulse generator 444 and the output 436 from black level clamping circuit 434 to produce a composite television-format output signal 450. Output amplifier 452 amplifies signal 450 to produce a television-format output signal 454 which may be distributed to television monitors and other devices which accept video signals. The signal 454 may be displayed on a monitor to show the position and selection status of each exposure sensor. Signal 454 is provided to a video mixer 456.

An image processor 490 receives image signals 132, 144 from imaging receptors 118, 134. Image signals 132, 144 may be in a television format, or may be in any other format produced by the imaging receptors 118, 134 and acceptable to the image processor. The image processor 490 provides image storage functions, including facilities for storing one or more recently acquired diagnostic images and allowing such image or images to be displayed even after the imaging energy source is turned off. These facilities are sometimes referred to as "last image hold." Image processor 490 may provide a variety of additional functions for manipulating and operating on images under control of examination personnel, such as filtering, integration of multiple images to reduce noise, and edge enhancement. The image processor 490 communicates with an imaging system controller 480 via signal paths 494, 496, allowing examining personnel to control the operation of image processor 490. The output of the image processor 490 is preferably a television format signal 456 which is provided to a video mixer 456.

Video mixer 456 selectably mixes (or overlays) signal 454, which represents the position and selection status of each of the exposure sensors, with image processor output signal 492 representing an acquired diagnostic image. The video mixer 456 provides an output signal 458 to monitor 460. When the non-overlayed image signal is selected, examining personnel may view the "plain" diagnostic image signal on monitor 460. When the overlayed image signal is selected, examining personnel may view on monitor 460 the diagnostic image signal with the sensor positions and selection status overlayed thereon. The overlayed signal shows the position of each sensor with respect to structures or features of the image. Examination personnel may use this information to determine which sensors should be selected to correspond to the structure or region of interest, or to determine whether an existing selection of sensors is appropriate.

The overall operation of the imaging system is preferably controlled by an imaging system controller 480, with which the ECS control element 112 cooperates. In imaging systems employing X-rays, the imaging system controller 480 is often referred to as an X-ray generator control. A suitable imaging system controller 480 for use in radiographic and fluoroscopic imaging applications in connection with the above-referenced imaging system components (X-ray tube 118, and image receptor 134) is commercially available from Continental X-Ray Corporation, 2000 S. 25th Avenue, Broadview, Ill. 60153 (the assignee of the present invention) under the designation TM GENERATOR. Other suitable controllers may be available, but it should be noted that X-ray generator controls (and other control devices for imaging systems) are typically designed for use with particular types, brands, and models of imaging equipment, and therefore, modifications may be required to adapt an imaging system controller to equipment for which it was not specifically designed.

The X-ray generator control 480 controls exposure parameters (including X-ray tube high voltage and other tube parameters), receives and displays information to the user relating to the examination, and performs other control and monitoring functions. The X-ray generator control 480 receives radiographic and fluoroscopic exposure requests from the user and forwards such request to ABS logic unit 384 via signal path 380 and to AEC logic unit 390 via signal path 388. These requests are also provided to variable gain amplifier 428 so that it may adjust the amplifier gain to correspond to the type of exposure (e.g. radiographic or fluoroscopic) being performed.

According to an aspect of the invention, the control element 112 provides facilities to allow examining personnel to select specific sensor elements or sensor locations to be used for exposure control. The examining personnel may, for example, select for use in exposure control those sensors or sensor locations which correspond to the structure or region of interest as portrayed in an acquired image. A remote control device 464, an area of interest selector unit 468, and a mode selector 484, cooperate with the imaging system controller 480 and the input signal analyzer 474 to allow examining personnel to select the exposure sensors to be used. The area of interest selector 468 provides a signal 470 to monitor 460 to display the location of each sensor and its selection status. Advantageously, the sensor positions may be viewed by examining personnel in a calibration, test, or set-up mode prior to operation, and thus prior to actual use of the sensors in exposure control. The area of interest selector unit 468 provides a signal 472 to input signal analyzer 474 to indicate to it which exposure sensors have been selected for use by examining personnel. Subject to rejection of one or more sensors because the sensor is producing out-of-range or otherwise spurious measurements, the input signal analyzer 474 communicates the selection of exposure sensors to preamplifier array 418 and analog switch array 428 via signal path 476.

In a manual selection mode, examining personnel may use remote control device 464 to select or deselect particular sensors. User control inputs to remote control device 464 are communicated via signal path 466 to the area of interest selector 468. As best seen in FIG. 6, the sensor positions and selection status (represented by items 320a, 320b, . . . 320y) may be displayed on monitor 460, overlayed upon an acquired diagnostic image 316 of the structure or region of interest. As best seen in FIG. 6, the symbols representing selected sensors 360b, 360c, 360d, 360g, 360h, 360i, 360m, 360r, and 360w, are preferably highlighted (shown in the figure by hatching) to indicate their selection. All other sensors are wholly or partially outside of the structure or region of interest 116 and are not selected. It will be appreciated that the by overlaying the sensor positions on an acquired image, the ECS 100, 100' allows examining personnel to easily determine which exposure sensors should be selected for use.

According to another aspect of the invention, the control element 112 provides facilities to receive from examining personnel a selection of an anatomical patient region to be examined, and in response thereto, selects appropriate sensors for use in exposure control during an examination of such a region. The imaging system controller 480 includes storage means 394 for storing characteristics of a plurality of anatomical patient regions (APR) which may be selected by examining personnel using an operator interface (not shown) provided by the imaging system controller 480.

The stored characteristics preferably include information describing the size or shape of a structure or region of interest (SRI) 116 associated with each APR, so that the imaging system controller 480 may initially select a set of exposure sensors corresponding to that SRI. Alternately, the stored characteristics may directly identify the exposure sensors to be initially selected for use in imaging the SRI 116 associated with each APR. The stored characteristics may also include recommended "technique" or exposure parameters (such as X-ray tube high-voltage and current settings, and exposure time limits), and relative patient/imaging system positioning or movement information, which may be associated with each APR. When the APR is selected, the initial selection of exposure sensors is preferably displayed to examining personnel so that changes to the selection may be made.

A mode selector 484 operates in cooperation with the imaging system controller 480 and the input signal analyzer 474 to enable examining personnel to choose between operation, test, and calibration modes. The imaging system controller 480 provides mode selection instructions to mode selector 484 via signal path 482. The mode selector 484 provides mode control signals via signal path 486 to the input signal analyzer 474. The input signal analyzer 474 responsively changes operating parameters of the preamplifier array 418 and other components to allow testing of the sensors and calibration and adjustment of the preamplifiers to normalize measurements made by each exposure sensor. Operation of the mode selector 484 is discussed further in connection with the method 510 of FIG. 5.

The ABS logic unit 384 receives processed image brightness information from the corresponding sensor array via lead 426. During a fluoroscopic exposure, if ABS has been enabled through the X-ray generator control 480, the ABS logic unit 384 compares the image brightness measured using selected sensors (i.e., at selected locations within the image field) with a predefined desired image brightness. ABS logic unit 384 provides instructions to the imaging system controller 480 to adjust exposure parameters as needed to approach and maintain the desired brightness. In imaging systems employing X-rays, the imaging system controller 480 is preferably an X-ray generator control and adjusts the high voltage supplied to X-ray tube 114 on lead 128 (and possibly other parameters) to achieve the desired brightness.

The AEC logic unit 390 receives processed image exposure information from the corresponding sensor array via lead 426. During a radiographic exposure, if AEC has been enabled through the imaging system controller 480, the AEC logic unit 390 compares the desired integrated exposure dose, measured using selected sensors (i.e., at selected locations within the image field) with a predefined desired exposure. AEC logic unit 390 provides instructions to the imaging system controller 480 to adjust exposure parameters as needed to achieve the desired exposure. In imaging systems employing X-rays, the imaging system controller 480 is preferably an X-ray generator control and terminates the radiographic exposure when the desired exposure amount (dose) has been reached.

FIG. 5 is a flow diagram showing a method 510 for use in conjunction with the control element 112 for controlling the ECS 100, 100'. The method starts at step 512 (FIG. 5a). Steps 512–524 are used to select one of three main operating modes: Calibration, Test/Set-Up, and Operation. In step 514, a test is made to determine whether the imaging system is in the Operation mode (as selected by examining personnel). If the imaging system is in the operation mode the method proceeds with step 524. If the imaging system is not in the operation mode, the method continues at step 516, in which the analog switch array 422 is enabled and operates from the TV sync pulse generator 444 (FIG. 4). Commercially available sensor arrays typically have a large number of sensor elements and only one or a small number of output signal leads on which the sensor outputs are multiplexed. Accordingly, the elements of the sensor array must be scanned in order to obtain measurements across the complete array. In the Calibration and Test/Set-Up modes, the analog switch array 422 is preferably driven from the TV sync pulse generator 444 to enable the array 422 to be scanned, and to allow display of the position of each sensor. In step 518, a test is made to determine whether the imaging system is in the Calibration mode. If the imaging system is in the Calibration mode, the method proceeds with step 520. If the imaging system is not in the Calibration mode, then the system is in the Test/Set-Up mode, and the method continues with step 522.

After entering the Calibration mode in step 520, step 526 (FIG. 5b) is executed, in which the outline of all exposure sensors is displayed on the monitor. In step 528, the imaging system controller 480 ensures that the imaging energy source is turned off. In step 530, all sensors in the exposure sensor array are scanned. Since the imaging energy source is off, the exposure measurement from each sensor represents the minimum value the sensor can produce, and is referred to as the "dark current." For each sensor, the input signal analyzer automatically sets the offset of the corresponding preamplifier to compensate for the sensor's dark current.

In step 532, an operator installs a homogeneous phantom in the imaging field. The homogeneous phantom is a test object of known uniform attenuation with respect to the imaging energy source. For example, if X-rays are used as the imaging energy source, the phantom exhibits a known, uniform radiographic density. Because the phantom has a known attenuation, it can be used to calibrate each sensor and the corresponding preamplifier, including compensating for variations in the sensitivity among the exposure sensors. The imaging system controller 480 enables the imaging energy source.

In step 534, all sensors in the exposure sensor array are again scanned. For each sensor, the input signal analyzer automatically sets the gain of the corresponding preamplifier to calibrate the sensor/preamplifier output to a known value.

Calibration is now complete, and the method returns to step 512 (FIG. 5a). After entering the Test/Set-Up mode in step 522, step 536 (FIG. 5c) is executed, in which all sensors in the exposure sensor array are scanned. In step 538, the image processor is instructed to display on the monitor a previously acquired diagnostic image using the last-image hold facility, and the video mixer overlays the outline of all exposure sensors.

In step 540, the imaging system controller 480 identifies the anatomical patient region (APR) most recently selected by examining personnel, and determines the associated imaging system control characteristics associated with that selection. The corresponding exposure sensors are selected, and the selected sensors are indicated on the display by highlighting or coloring their symbol or outline. In step 542, examining personnel may indicate or edit the structure or region of interest by selecting or deselecting appropriate sensors using the remote control device 464.

Also in step 542, examining personnel may optionally select the manner in which measurements from one or more sensors are weighted or aggregated for use in controlling or terminating an exposure. For example, in an "averaging" mode, the exposure control system may be directed to use the average of measurements from a plurality of selected sensors to control or terminate an exposure. Alternatively, in a "race" mode, the exposure control system may be directed to use the measurement from the particular sensor (or group thereof), among those which have been selected, that happens to produce the largest exposure measurement value (or several high-output-value sensors), in order to avoid overexposing any particular portion of the image. In the "race" mode, the sensor (or group of sensors) which most rapidly accumulates exposure effectively dominates the operation of the exposure control system. Other sensor weighting or aggregation modes could also be defined. Moreover, the particular weighting or aggregation mode used for an examination could also be selected automatically, based on predefined parameters, or according to the current anatomical patient region. The Test/Set-Up mode is now complete, and the method returns to step 512 (FIG. 5a).

After entering the Operation mode in step 524, step 544 (FIG. 5d) is executed, in which the analog switch array selects only the exposure sensors which have been preselected via the Test/Set-Up mode discussed previously. In step 546, the imaging system controller 480 tests to determine whether an exposure has been requested. If an exposure has not been requested, the method returns to step 512 (FIG. 5a) to await an exposure request or a change in the operating mode. If an exposure has been requested, the method continues in step 548, in which the imaging system controller 480 tests to determine whether the type of requested exposure is a still exposure (i.e., film, photospot, or the like) or a continuous, real-time, or near-real-time exposure (i.e., fluoroscopy). If the requested exposure is a still exposure, the method jumps to step 566.

If the requested exposure is not a still exposure, the method continues in step 550, in which fluoroscopy mode is enabled (or maintained). In step 554, the imaging system controller 480 activates the ABS logic. The ABS logic implements the appropriate sensor weighting or aggregation mode, which may have been manually selected by examining personnel or automatically selected by the system. In step 556, the system determines an average value of exposure measurement signals exclusively from selected sensors. In step 558, the ABS logic unit 384 determines appropriate control inputs (generator parameters) for the imaging system controller 480 to cause imaging receptor brightness to approach and maintain a predetermined desired level. The imaging system controller 480 controls the exposure according to the control signal from the ABS logic unit 384. In step 560, the master gain of amplifier 428 is increased to produce from the majority of the selected sensors an output level which is within a desired range. The gain must generally be increased because continuous or lengthy exposures (including, for the purpose of this discussion, both continuous and pulsed fluoroscopy) are normally performed at low exposure rates. In step 562, the input signal analyzer deselects sensors having outputs outside of a predefined range of valid inputs. In effect, sensors with measurements that appear to be "too bright" or "too dark" are rejected.

In step 564, the ABS logic unit 384 continues to determine appropriate control inputs (generator parameters) to cause the desired exposure level, and the imaging system controller 480 "fine-tunes" the exposure according to the control signal from the ABS logic unit 384. The method then returns to step 512 (FIG. 5*a*), repeating until the Operation mode is terminated.

If, in step 548, the system controller 480 determines that the requested exposure is a still exposure (i.e., film, photospot, or the like) the method jumps to step 566. In step 560, the imaging system controller 480 enables the AEC logic unit 390. The AEC logic implements the appropriate sensor weighting or aggregation mode, which may have been manually selected by examining personnel or automatically selected by the system. In step 568, the master gain of amplifier 428 is reduced to produce from the majority of the selected sensors an output level which is within a desired range. The gain must generally be reduced because still exposures (including radiographic film and "photospot" exposures) are normally performed at high exposure rates.

In step 570, the input signal analyzer deselects sensors having outputs outside of a predefined range of valid inputs during the initial phase of the exposure. In effect, sensors with measurements that appear to be "too bright" or "too dark" are rejected. In step 572, when the desired exposure is reached, the AEC logic unit 390 provides a control signal to imaging system controller 480 to terminate the exposure. The method then returns to step 512 (FIG. 5*a*), repeating until the Operation mode is terminated.

The above-described embodiments of the invention are merely examples of ways in which the invention may be carried out. Other ways may also be possible, and are within the scope of the following claims defining the invention.

What is claimed is:

1. An exposure control system for use with a diagnostic imaging system comprising:

an imaging receptor having a region receptive to imaging energy;

an imaging energy source directed toward said imaging receptor;

exposure control means coupled to said imaging energy source;

said imaging energy source having an output responsive to said exposure control means;

a plurality of sensors responsive to imaging energy to measure imaging energy exposure at respective predefined locations of said region;

means for defining a first portion of said region as of diagnostic interest;

display means for displaying for each of said plurality of sensors a position of said respective predefined location of said region to which such sensor is responsive; and means for selecting for use only sensors responsive to measure imaging energy exposure at said respective predefined locations which are within said first portion of said region;

said exposure control means being responsive to said selected sensors to control said output of said imaging energy source accordingly.

2. An exposure control system for use with a diagnostic imaging system comprising:

an imaging receptor having a region receptive to imaging energy;

an imaging energy source directed toward said imaging receptor;

exposure control means coupled to said imaging energy source;

said imaging energy source having an output responsive to said exposure control means;

a plurality of sensors responsive to imaging energy to measure imaging energy exposure at respective predefined locations of said region;

means for defining a first portion of said region as of diagnostic interest;

means for defining a normal range of output values associated with said plurality of sensors; and means for comparing an output value of at least one of said plurality of sensors with said normal range of output values and for selecting such sensor for use only if said output value is within said normal range.

said exposure control means being responsive to said selected sensors to control said output of said imaging energy source accordingly.

3. The exposure control system of claims 1 or 2 wherein said exposure control means is an automatic brightness system.

4. The exposure control system of claims 1 or 2 wherein said exposure control means is an automatic exposure control system.

5. The exposure control system of claims 1 or 2 wherein said imaging energy source is an X-ray tube.

6. The exposure control system of claims 1 or 2 wherein said imaging receptor is X-ray film.

7. The exposure control system of claims 1 or 2 wherein said imaging receptor is a substantially flat X-ray flux sensitive layer.

8. The exposure control system of claims 1 or 2 wherein at least one of said plurality of sensors comprises an ion chamber disposed between said imaging receptor and said imaging source.

9. The exposure control system of claims 1 or 2 wherein at least one of said plurality of sensors comprises a radiation detector disposed between said imaging receptor and said imaging source.

10. The exposure control system of claims 1 or 2 wherein at least one of said plurality of sensors comprises a phototransistor disposed between said imaging receptor and said imaging source.

11. The exposure control system of claims 1 or 2 wherein at least one of said plurality of sensors comprises a photodiode disposed between said imaging receptor and said imaging source.

12. The exposure control system of claims 1 or 2 wherein at least one of said plurality of sensors comprises a fluorescent material disposed between said imaging receptor and said imaging source, and an optical light detector responsive to light produced by said fluorescent material.

13. The exposure control system of claims 1 or 2 wherein said predefined locations are disposed substantially uniformly across said region, and each of said plurality of sensors is disposed substantially adjacent to a respective one of said predefined locations.

14. The exposure control system of claim 13 wherein each of said plurality of sensors is an ion chamber.

15. The exposure control system of claims 1 or 2 wherein said predefined locations are disposed substantially uniformly across said region, said plurality of sensors is formed as a regular array of sensor elements, and each of said sensor elements are disposed substantially adjacent to a respective one of said predefined locations.

16. The exposure control system of claim 15 wherein each of said plurality of sensors is an ion chamber.

17. The exposure control system of claims 1 or 2 wherein said imaging receptor comprises an image intensifier.

18. The exposure control system of claims 1 or 2 wherein said imaging receptor comprises means responsive to said imaging energy incident thereon to produce an image.

19. The exposure control system of claims 1 or 2 wherein said imaging receptor comprises means responsive to said imaging energy to emit light in an amount related to an amount of imaging energy incident on said receptor.

20. The exposure control system of claim 19 wherein said predefined locations are disposed substantially uniformly across said region, and each of said plurality of sensors is disposed substantially adjacent to a location on said light emitting means corresponding to a respective one of said predefined locations.

21. The exposure control system of claim 19 wherein said predefined locations are disposed substantially uniformly across said region, said plurality of sensors is formed as a regular array of sensor elements, and each of said plurality of sensor elements is disposed substantially adjacent to a location on said light emitting means corresponding to a respective one of said predefined locations.

22. The exposure control system of claims 1 or 2 wherein said means for defining a first portion of said region as of diagnostic interest comprises means operable by a user for indicating which sensors correspond to locations within said portion of diagnostic interest.

23. The exposure control system of claims 1 or 2 wherein:
    each of said plurality of sensors produces a respective exposure output value;
said exposure control system further comprising:
    means for defining a normal range for said exposure output value; and
    means responsive to said exposure output value from each sensor for selecting such sensor for use only if said exposure output value is within said normal range.

24. The exposure control system of claims 1 or 2 further comprising:
    means for defining a plurality of anatomical patient regions;
    means for storing for each of said defined anatomical patient regions a definition of an associated region of diagnostic interest;
    and user operable means for selecting one of said defined anatomical patient regions;
    wherein said means for defining a first portion of said region as of diagnostic interest employs said definition stored for said selected anatomical region.

25. The exposure control system of claims 1 or 2, wherein:
    each sensor exhibits a response characteristic when exposed to said imaging energy; and
    said exposure control system further comprises adjusting means responsive to each of said plurality of sensors for producing an adjusted output signal for such sensor such that after adjustment said response characteristic exhibited by each sensor is substantially the same as said response characteristic exhibited by all other sensors.

26. An exposure control system for use with a diagnostic imaging system comprising:
    an imaging receptor having a region receptive to imaging energy;
    an imaging energy source directed toward said imaging receptor;
    exposure control means coupled to said imaging energy source;
    said imaging energy source having an output responsive to said exposure control means;
    a plurality of sensors responsive to imaging energy to measure imaging energy exposure at respective predefined locations of said region;
    means for defining a first portion of said region as of diagnostic interest;
    means for defining a normal range of output values associated with said plurality of sensors;
    means for comparing an output value of at least one of said plurality of sensors with said normal range of output values and for selecting such sensor for use onlu if said output value is within said normal range;
    display means for displaying an image acquired by said imaging receptor; and
    means cooperating with said display means for presenting thereon for each of said plurality of sensors and indicia of a position with respect to said image of said respective predefined location of said region to which such sensor is responsive;
    said exposure control means being responsive to said selected sensors to control said output of said imaging energy source accordingly.

27. For use in an exposure control system for a diagnostic imaging system; the imaging system having an imaging energy source; the exposure control system having a plurality of exposure sensors, and means for adjusting an output level for each of the plurality of sensors, the adjusting means including an offset parameter and a gain parameter; a calibration method comprising the steps of:
    (a) operating each sensor with the imaging energy source disabled;
    (b) measuring a dark output value for each sensor;
    (c) controlling the offset parameter of the adjusting means for each sensor responsive to the dark current value to null the output level from such sensor when said imaging energy source is disabled;
    (d) operating each sensor with the imaging energy source enabled and producing a predefined imaging energy output level;
    (e) measuring an calibration output value for each sensor; and
    (f) controlling the gain parameter of the adjusting means for each sensor responsive to the calibration output value to cause the output level from such sensor to equal a predefined output value when said imaging energy source is enabled.

28. An exposure control system for use with a diagnostic imaging system comprising:

X-ray imaging receptor having a region receptive to X-rays;

an X-ray source directed toward said X-ray imaging receptor;

exposure control means coupled to said X-ray source;

said X-ray source having an output responsive to said exposure control means;

a plurality of sensors responsive to X-rays to measure X-ray exposure at respective predefined locations of said region;

means for defining a first portion of said region as of diagnostic interest;

display means for displaying for each of said plurality of sensors a position of said respective predefined location of said region to which such sensor is responsive; and means for selecting for use only sensors responsive to measure X-ray exposure at said respective predefined locations which are within said first portion of said region;

said exposure control means being responsive to said selected sensors to control said output of said X-ray source accordingly.

29. An exposure control system for use with a diagnostic imaging system comprising:

an imaging receptor having a region receptive to imaging energy:

an imaging energy source directed toward said imaging receptor;

exposure control means coupled to said imaging energy source;

said imaging energy source having an output responsive to said exposure control means;

a plurality of sensors responsive to imaging energy to measure imaging energy exposure at respective predefined locations of said region;

means for defining a first portion of said region as of diagnostic interest;

display means for displaying for each of said plurality of sensors a position of said respective predefined location of said region to which such sensor is responsive;

means for selecting for use only sensors responsive to measure imaging energy exposure at said respective predefined locations which are within said first portion of said region;

said exposure control means being responsive to said selected sensors to control said output of said imaging energy source accordingly; and means cooperating with said display means for displaying for each of said plurality of sensors an indication of whether such sensor is selected for use.

30. An exposure control system for use with a diagnostic imaging system comprising:

an imaging receptor having a region receptive to imaging energy;

an imaging energy source directed toward said imaging receptor;

exposure control means coupled to said imaging energy source;

said imaging energy source having an output responsive to said exposure control means;

a plurality of sensors responsive to imaging energy to measure imaging energy exposure at respective predefined locations of said region;

means for defining a first portion of said region as of diagnostic interest;

means for defining a normal range of output values associated with said plurality of sensors;

means for comparing an output value of at least one of said plurality of sensors with said normal range of output values and for selecting such sensor for use only if said output value is within said normal range;

said exposure control means being responsive to said selected sensors to control said output of said imaging energy source accordingly; and means cooperating with a display means for displaying for each of said plurality of sensors an indication of whether such sensor is selected for use.

31. An exposure control system for use with a diagnostic imaging system comprising:

an imaging receptor having a region receptive to imaging energy:

an imaging energy source directed toward said imaging receptor;

exposure control means coupled to said imaging energy source;

said imaging energy source having an output responsive to said exposure control means;

a plurality of sensors responsive to imaging energy to measure imaging energy exposure at respective predefined locations of said region;

means for defining a first portion of said region as of diagnostic interest;

display means for displaying an image acquired by said imaging receptor;

means cooperating with said display means for presenting thereon for each of said plurality of sensors an indicia of a position with respect to said image of said respective predefined location of said region to which such sensor is responsive;

means for selecting for use only sensors responsive to measure imaging energy exposure at said respective predefined locations which are within said first portion of said region;

said exposure control means being responsive to said selected sensors to control said output of said imaging energy source accordingly.

32. The exposure control system of claim 31, further comprising:

means cooperating with said display means for each of said plurality of sensors an indication of whether such sensor is selected for use.

* * * * *